United States Patent [19]

Jouannetaud et al.

[11] 4,447,660

[45] May 8, 1984

[54] PROCESS FOR THE ISOMERIZATION OF ORTHO-AND PARA-BROMOPHENOLS OR THE ETHERS THEREOF INTO META-BROMOPHENOLS AND CORRESPONDING ETHERS

[75] Inventors: Marie-Paule Jouannetaud; Jean-Pierre Gesson; Jean-Claude Jacquesy, all of Poitiers, France

[73] Assignee: PCUK Produits Chimiques Ugine Kuhlmann, Courbevoie, France

[21] Appl. No.: 428,677

[22] Filed: Sep. 30, 1982

Related U.S. Application Data

[63] Continuation of Ser. No. 267,415, May 26, 1981, abandoned.

[30] Foreign Application Priority Data

Jun. 3, 1980 [FR] France ............................. 80 12262

[51] Int. Cl.$^3$ ............................................. C07C 39/27
[52] U.S. Cl. ................................. 568/774; 568/656; 568/676; 568/768; 568/771
[58] Field of Search ............... 568/774, 771, 768, 676, 568/677, 656

[56] References Cited

U.S. PATENT DOCUMENTS 3,681,467  8/1972  O'Bara ............................. 568/774
4,138,411  2/1979  Gandihon ......................... 568/774

FOREIGN PATENT DOCUMENTS 784782  5/1968  Canada ............................. 568/779

OTHER PUBLICATIONS

Jacquessy et al., "J.C.S. Chem. Comm." (1980) p. 100–111.

Fury et al., "J. Org. Chem." (Jul. 1965) vol. 30, pp. 2301–2304.

Primary Examiner—Werren B. Lone
Attorney, Agent, or Firm—Pennie & Edmonds

[57] ABSTRACT

Process for the isomerization of ortho- and para-bromophenols or the ethers thereof into corresponding meta-brominated derivatives by isomerizing ortho- and para-bromophenols in the corresponding ethers in the presence of a liquid superacid at a temperature in the region of ambient temperature.

6 Claims, No Drawings

PROCESS FOR THE ISOMERIZATION OF ORTHO-AND PARA-BROMOPHENOLS OR THE ETHERS THEREOF INTO META-BROMOPHENOLS AND CORRESPONDING ETHERS

This is a continuation of application Ser. No. 267,415, filed May 26, 1981, now abandoned.

TECHNICAL FIELD

This invention relates to a process for the isomerization of ortho- and para-bromophenols and the phenol ethers thereof into meta-bromophenols and meta-bromophenol ethers.

BACKGROUND ART

It is well known that the halogenation of phenols and their ethers occurs essentially at the ortho and para positions relative to the phenol or phenol ether group. Substitution at the meta position by halogen is regarded as difficult and it is usually necessary to adopt indirect methods which involve a number of reaction steps and are therefore expensive. However, meta-bromophenols and their ethers are known to be useful products for the chemical industry, as they may be used, in particular, as intermediate products in the manufacture of bactericides and insecticides, in the preparation of resins by condensation with formaldehyde for providing a crease-resistant finish for textiles, and in the preparation of lubricants, hydraulic fluids, etc.

Recently, it has been shown by J. C. Jacquesy, M. P. Jouannetaud and S. Makani (J. CHEM. SOC., CHEM. COMM., 1980, 110-111) that bromination of para-cresols, 2,4- or 3,4-xylenols and the ethers thereof, in a superacidic medium (HF—SbF$_5$), at low temperature ($-45°$ C.), leads to good yields of derivatives which are brominated at the meta position of the phenol or ether function. Under the conditions used by these authors, ordinary phenol and ortho- and meta-cresol essentially yield para-brominated derivatives. The article mentioned above also states that the formation of meta-brominated derivatives, in the case of the para-cresols and xylenols or their ethers, does not result from any isomerization of ortho- or para-brominated compounds since, for example, 2-bromo-4-methylphenol or 4-bromo-2,6-dimethylphenol or the ethers thereof are recovered unchanged when treated with a superacid HF—SbF$_5$ at $-45°$ C.

DISCLOSURE OF THE INVENTION

Totally unexpectedly, the applicants have now found that if ortho- or para-brominated derivatives of phenols or phenol ethers are treated with a liquid superacid at temperatures in the region of ambient temperature, these derivatives are isomerized, often with excellent yields, to form meta-brominated derivatives.

Although it is advantageous to carry out the reaction at ambient temperature since heat need not be added or taken away, the process is operable at other temperatures. Complete parameters of the operable temperature range have not been established and a temperature should be employed which will cause isomerization of alpha- and para-bromophenols or ethers to the meta-brominated derivative which can be determined by routine experimentation. Although ambient temperature generally ranges from between about 18° and 24° C., temperatures in the range of about 10° to 30° C. may also be used.

By liquid superacids, we mean complexes which are liquid in the region of ambient temperature, such as, for example, "magic acid" FSO$_3$H—SbF$_5$, fluoroantimonic acid HF—SbF$_5$ or the complex of trifluoromethanesulfonic acid and antimony pentafluoride, CF$_3$SO$_3$H—SbF$_5$. These superacids have $H_o$ acidities, estimated on the Hammett logarithmic scale of about $-25$, whereas the acidity of 100% sulfuric acid is only $-11$ and that of 100% hydrofluoric acid is only $-10$. The acidities of liquid superacids are therefore up to $10^{14}$ higher than the acidities of conventional strong inorganic acids.

The isomerization of ortho- or para-brominated derivatives of phenols or their ethers with these liquid superacids is very easily carried out by contacting the brominated derivative with a sufficient quantity of superacid to provide a homogeneous medium. The reaction time may vary from about one hour to several days. With certain phenol ethers, isomerization into the meta form is accompanied by partial splitting of the ether function, with formation of the corresponding phenol.

The reaction seems to be specific to brominated derivatives since, under the same conditions, the corresponding chlorinated derivatives do not undergo any isomerization, only sometimes the chlorine atom is eliminated, particularly at elevated temperature.

The following non-restrictive examples illustrate various aspects of the invention:

EXAMPLE 1

2.9 mmol of parabromo-anisole and 15 cm$^3$ of 1.7 M HF—SbF$_5$ superacid are contacted for 55 hours at ambient temperature in a poly(tetrafluoroethylene) container. Chromatographic analysis of the reaction products shows that a mixture of meta-bromo-phenol (25%) and meta-bromoanisole (40%) is formed, in a 65% yield.

EXAMPLE 2

The method is as in Example 1, but using 2.9 mmol of parabromo-phenol. The reaction is almost complete after 24 hours of. After 48 hours reaction at ambient temperature, 90% of meta-bromo-phenol is formed.

EXAMPLE 3

The method is as in Example 1, but using 2.9 mmol of 3-methyl-4-bromophenol. After 48 hours of reaction at ambient temperature, 80% of 3-methyl-5-bromophenol is formed.

EXAMPLE 4

The method is as in Example 1, but using 2.9 mmol of ortho-bromophenol and limiting the reaction time to 8 hours at ambient temperature. Analysis of the reaction medium shows that 13% of unconverted ortho-bromophenol remain and that 4% of parabromophenol and 28% of meta-bromophenol is formed.

EXAMPLE 5

A mixture of 2.9 mmol of parabromophenol and 15 g of hydrofluoric acid previously saturated with BF$_3$ at $-40°$ C. is left in contact for 24 hours at ambient temperature. Analysis shows that 22% of uncoverted parabromophenol is left and that:
 3 to 4% of meta-bromophenol,
 50% of phenol, and
 24% of dibrominated phenol is formed.

EXAMPLE 6

The method is as in Example 1, but using 2.9 mmol of ortho-bromoanisole. After 60 hours of reaction at ambient temperature, 27% of meta-bromoanisole and 37% of meta-bromophenol is obtained.

We claim:

1. A process for the isomerization of ortho- and para-bromo phenols or the ethers thereof into corresponding meta-brominated derivatives, comprising isomerizing the ortho- or para-brominated phenols or ethers in the presence of a liquid superacidic medium having a $H_0$ acidity estimated on the Hammett logarithmic scale of greater than $-11$ up to about 31 25 at elevated temperatures to effect isomerization of the ortho- and para-bromophenols or the corresponding ethers to the meta-brominated derivatives.

2. The process according to claim 1 in which the temperature is ambient temperature.

3. The process according to claims 1 or 2 in which the liquid superacidic medium is fluoroantimonic acid $HF-SbF_5$.

4. The process according to claims 1 or 2 in which the liquid superacidic medium is a complex of hydrofluoric acid and boron trifluoride $HF-BF_3$.

5. The process according to claim 1 in which the liquid superacidic medium is magic acid $FSO_3H-SbF_5$.

6. The process according to claim 1 in which the liquid superacidic medium is a complex of trifluoromethanesulfonic acid and antimony pentafluoride.

* * * * *

UNITED STATES PATENT AND TRADEMARK OFFICE
CERTIFICATE OF CORRECTION

PATENT NO. : 4,447,660
DATED : May 8, 1984
INVENTOR(S) : Marie-Paule Jouannetaud et al.

It is certified that error appears in the above—identified patent and that said Letters Patent is hereby corrected as shown below:

Column 3, line 15, reads "3125", should read -- -25 --

Signed and Sealed this

Twenty-ninth Day of January 1985

[SEAL]

Attest:

DONALD J. QUIGG

Attesting Officer

Acting Commissioner of Patents and Trademarks